US00PP31948P2

(12) United States Plant Patent
Van Swieten

(10) Patent No.: US PP31,948 P2
(45) Date of Patent: Jul. 7, 2020

(54) ***PHALAENOPSIS* ORCHID PLANT NAMED 'PHALFOTJ'**

(50) Latin Name: ***Phalaenopsis* hybrid**
Varietal Denomination: PHALFOTJ

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,801

(22) Filed: Jun. 7, 2019

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on phalaenopsis plant named, 'PHALFOTJ', QZ PBR 53002, filed Apr. 24, 2018.*

* cited by examiner

*Primary Examiner* — Anne Marie Grunberg
(74) *Attorney, Agent, or Firm* — Jondle & Associates, P.C.

(57) ABSTRACT

A new and distinct variety of *Phalaenopsis* plant named 'PHALFOTJ', particularly characterized by having reddish-purple flowers with reddish-purple lips, 1 to 2 peduncles that are medium long and sturdy, leaves that are oblong, and is propagated by meristem tissue culture, is disclosed.

3 Drawing Sheets

Genus and species: *Phalaenopsis* hybrid.
Variety denomination: 'PHALFOTJ'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALFOTJ'.

The new *Phalaenopsis* plant is a product of a planned breeding program conducted by the inventor in Bleiswijk, the Netherlands. The objective of this breeding program was to create a new *Phalaenopsis* plant with numerous attractive reddish-purple flowers with reddish-purple lips, suitable for potted plant production.

The new *Phalaenopsis* plant 'PHALFOTJ' is a result of cross-pollination made by the inventor in November 2007 in Bleiswijk, the Netherlands, of the proprietary female, or seed parent, *Phalaenopsis* hybrid '01-1698' (unpatented) with the proprietary male, or pollen parent, *Phalaenopsis* hybrid '20421-01' (unpatented).

The new *Phalaenopsis* was selected by the inventor as a single plant within the progeny of the stated cross-pollination in a controlled greenhouse in Bleiswijk, the Netherlands, in November 2010. Asexual reproduction of the new *Phalaenopsis* plant by meristem tissue culture since 2013 in Bleiswijk, the Netherlands, has demonstrated that the new variety reproduces true to type with all of the characteristics, as herein described, firmly fixed and retained through successive generations.

Plant Breeder's Rights for this variety have been applied for in Europe on Apr. 24, 2018, by Applicant who obtained the subject matter disclosed directly from the Inventor. 'PHALFOTJ' has not been made publicly available or sold anywhere in the world more than one year prior to the effective filing date of this application.

SUMMARY OF THE INVENTION

The following are the most outstanding and distinguishing characteristics of this new cultivar when grown under normal horticultural practices in Bleiswijk, the Netherlands, and can be used to distinguish 'PHALFOTJ' as a new and distinct variety of *Phalaenopsis* plant:

1) Reddish-purple flowers with reddish-purple lips;
2) 1 to 2 peduncles;
3) Peduncle is medium long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 46-week-old plants in February 2019. Colors in the photographs may differ from the color values cited in the detailed botanical description, which accurately describe the actual colors of the new variety.

DESCRIPTION OF THE NEW VARIETY

Figure 1:
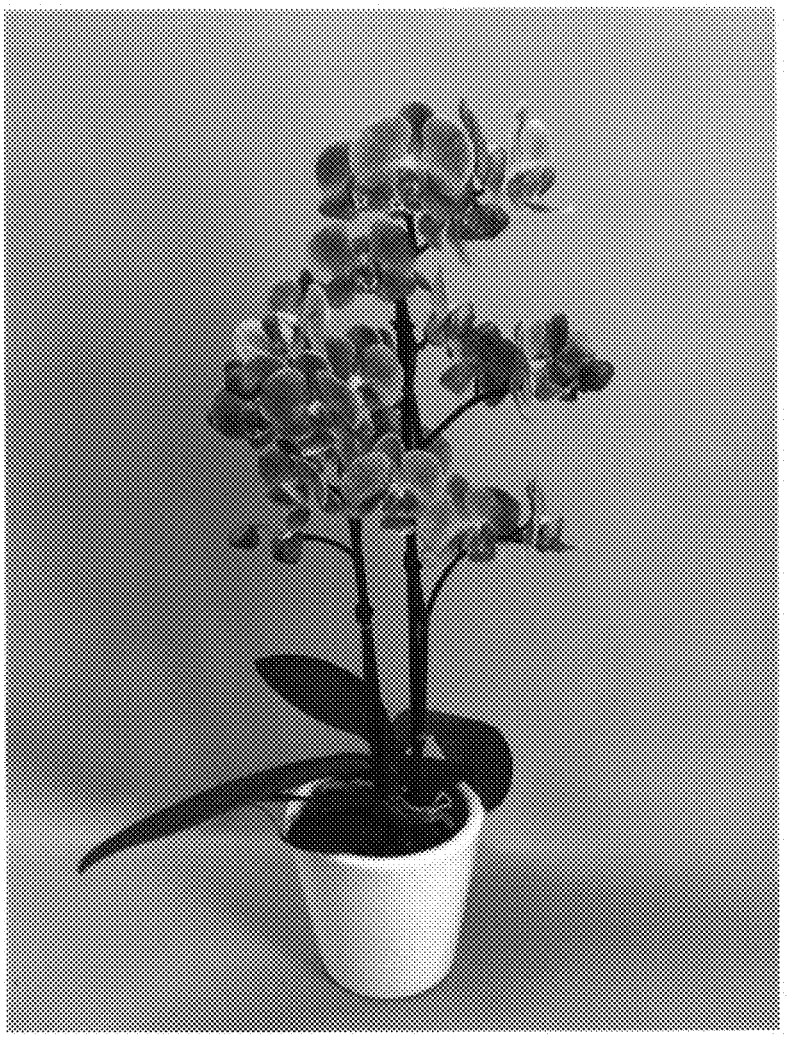
FIG. 1 shows the overall plant habit, including blooms, buds, and foliage of 'PHALFOTJ'.
Figure 2:
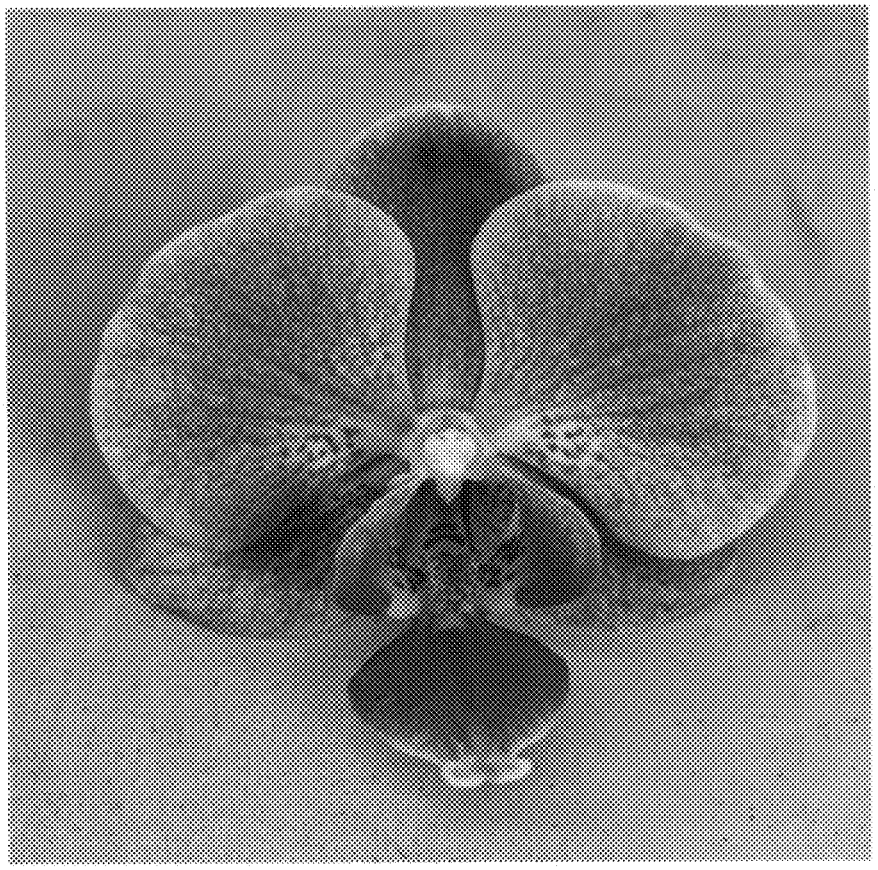
FIG. 2 shows a close-up of a flower of 'PHALFOTJ'.
Figure 3:
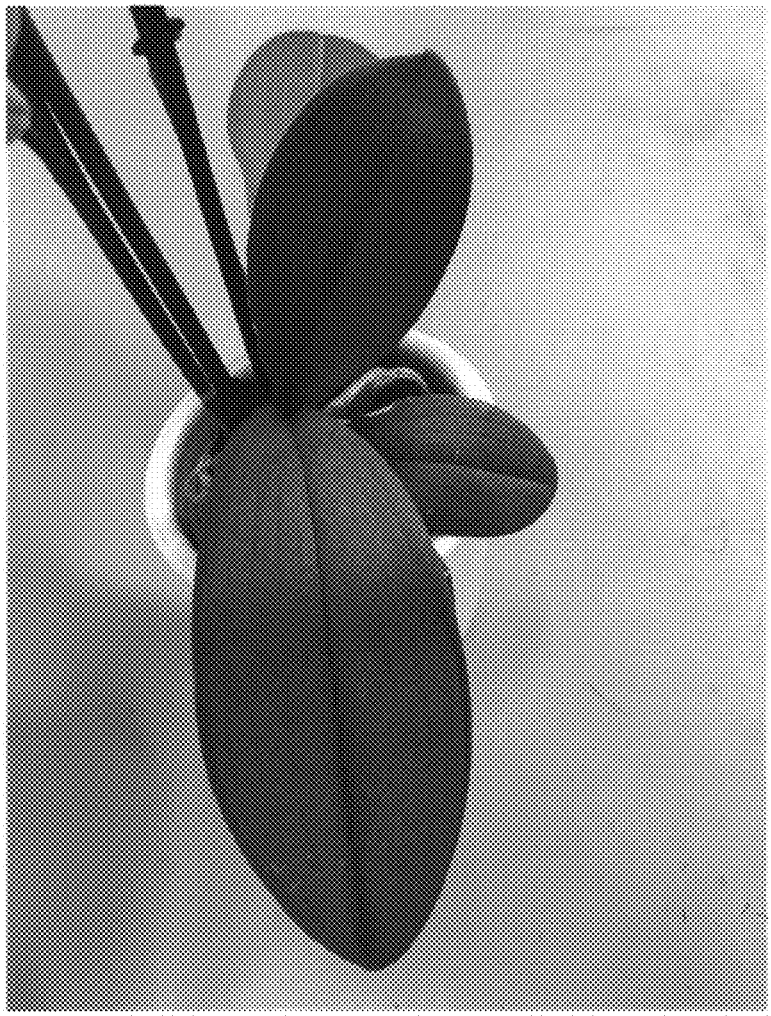
FIG. 3 shows an overhead view of the leaves of 'PHALFOTJ'.

The following detailed description sets forth the distinctive characteristics of 'PHALFOTJ'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2019 on flowering plants which were planted in 9-centimeter (diameter) pots. After in-vitro propagation, the plants were grown in nursery trays for 18-20 weeks, followed by transplantation to 9-centimeter pots and grown in a greenhouse between 27° C. to 29° C. for 25 weeks, continued by a cooling period of 6 weeks between 18° C. to 20° C. and 11 weeks in a greenhouse of 21° C. Flowering occurs after 42 weeks in 9-centimeter pots.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHALFOTJ'.

Parentage:
- *Female parent*.—*Phalaenopsis* cultivar '01-1698' (unpatented).
- *Male parent*.—*Phalaenopsis* cultivar '20421-01' (unpatented).

Propagation:
- *Type*.—Meristem tissue culture.

Roots:
- *Root description*.—Greyed-green (between RHS 190B and 190C) colored roots with branching lateral roots having yellow-green (RHS 195B) and slightly dark pink (RHS 182D) colored root tips.

Plant:
- *Commercial crop time to flowering*.—Following asexual propagation (in-vitro), the rooted cuttings grow for 18-20 weeks. After transplantation into 9-cm pots, the plants are finished after 40 to 42 weeks.
- *Growth habit of peduncle*.—Upright to slightly pendant with panicle inflorescence.
- *Height (from soil level to top of inflorescence)*.—Approximately 29.0 cm to 39.0 cm.
- *Width (measured from leaf tips)*.—About 32.0 cm to 34.0 cm.
- *Vigor*.—Moderate.

Leaves:
- *Mature leaves*.—Quantity per plant: 7 to 9 leaves are produced before flowering. Length (fully expanded): 16.0 cm to 18.0 cm. Width: 6.0 cm to 7.0 cm. Shape: Oblong. Base shape: Moderately elongated. Apex: Obtuse unequal. Leaf blade angle with the petiole (measured from the horizontal position): Between 15 degrees and 30 degrees. Leaf margin: Entire. Color: Upper surface: RHS 147A. Lower surface: RHS 147B and slightly dark red (RHS 187A) at the margin. Texture (upper surface): Rough. Thickness: 1.8 mm to 2.0 mm. Venation: Pattern: Parallel. Color of the midvein: Upper surface: RHS 147A. Lower surface: Between RHS 187A and 187B (darker at the base and diluting toward the tip).

Peduncle:
- *Quantity per plant*.—1 to 2.
- *Number of flowers per peduncle*.—12 to 22.
- *Length*.—29.0 cm to 39.0 cm.
- *Diameter*.—4.0 mm to 5.0 mm.
- *Strength*.—Strong.
- *Aspect*.—Upright to slightly pendant.
- *Texture*.—Smooth.
- *Color*.—Mix of yellow-green (RHS 146B) and brown (RHS 200B) (more green at the base).
- *Internode length*.—4.0 cm to 6.0 cm.

Inflorescence description:
- *Appearance*.—Upright to slightly pendant, panicle inflorescence with bilaterally symmetrical flowers that open in succession beginning with the lowermost flower.
- *Inflorescence size*.—Height (from base to tip): 220.0 mm to 270.0 mm.
- *Flowering time*.—First flowers can be expected 7 to 8 months after planting in a 9-cm pot.
- *Flower*.—Height: 48.0 mm to 50.0 mm. Diameter: 57.0 mm to 62.0 mm. Depth of lip: 17.0 mm to 19.0 mm.
- *Flower longevity*.—On the plant: 7 to 14 weeks.
- *Fragrance*.—Absent.
- *Flower bud*.—Average size: Medium. Length: 16.0 mm to 18.0 mm. Width: 15.0 mm to 17.0 mm. Shape: Round. Color: Light yellow-green (RHS 144D) at the base; light purplish-red (RHS N77B).
- *Petals*.—Arrangement: Open/free. Shape: Semi-circular. Apex: Rounded asymmetric. Margin: Slightly wavy. Length (from base to tip): 24.0 mm to 26.0 mm. Width: 31.0 mm to 33.0 mm. Color (when fully opened): Upper surface: Basic color: Light purple (RHS 76A). Over color: Reddish-purple shade and dots (RHS N78B) at the base. Lower surface: Basic color: Very light purple (RHS 76B). Over color: Purplish-pink (RHS N78C).
- *Dorsal sepal*.—Shape: Elliptic. Apex: Obtuse symmetric. Margin: Entire. Length (from base to tip): 26.0 mm to 28.0 mm. Width: 20.0 mm to 22.0 mm. Color (when fully opened): Upper surface: Basic color: Reddish-purple (between RHS N78A and N78B). Over color: Slightly light purple (RHS 76A) at the base. Lower surface: Basic color: Purplish-pink (RHS N78C). Over color: Light yellow-green (between RHS 195A and 195B).
- *Lateral sepals*.—Shape: Ovate. Apex: Obtuse asymmetric. Margin: Entire. Length (from base to tip): 27.0 mm to 29.0 mm. Width: 19.0 mm to 21.0 mm. Color (when fully opened): Upper surface: Basic color: Purplish-pink (RHS N78C). Over color: Light yellow-green (RHS 145C) at the base; spotted (RHS 59A). Lower surface: Basic color: Light reddish-purple (RHS N78D). Over color: Light green (RHS 145C) at the base; reddish-purple main vein (RHS N78A) toward apex.

*Labellum* (*lip*).—Whiskers: Present. Length of whiskers: 6.0 mm to 8.0 mm. Color of whiskers: White (RHS NN155C) with purplish-pink stripe (RHS N78C) at the base. Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Wavy. Length: 17.0 mm to 19.0 mm. Width: 9.0 mm to 11.0 mm. Color: Light yellow-green (RHS 155A) at the base; dark red stripes (RHS 183B) at the base; red (RHS 184B) on one side; reddish-purple (RHS N78B) toward other side.

*Apical lobe*.—Shape: Rhombic. Margin: Entire. Length: 18.0 mm to 20.0 mm. Width: 16.0 mm to 18.0 mm. Color: Slightly greenish-yellow (RHS 151B) at the base; red (RHS 184B) and reddish-purple (RHS N78B) toward whiskers.

*Callus*.—Average size: Small to medium. Height: 5.0 mm to 6.0 mm. Length: 4.0 mm to 5.0 mm. Width: 3.0 mm to 4.0 mm. Color: Yellow (RHS 9A); dotted (RHS 183B).

Reproductive organs:

*Column*.—Length: 7.0 mm to 9.0 mm. Diameter: 4.8 mm to 5.1 mm. Color: White (RHS NN155C) with a touch of reddish-purple (RHS N78B) toward the top.

*Pollinia*.—Quantity: 2. Diameter: 0.8 mm to 1.0 mm. Color: Orange (RHS 25A).

*Ovary*.—Length: 8.0 mm to 10.0 mm. Diameter: 2.0 mm to 2.2 mm. Color: Light yellow-green (RHS 145A to 145C) toward the flower.

*Pedicel*.—Length: 29.0 mm to 31.0 mm. Diameter: 2.2 mm to 2.4 mm. Color: Green (RHS 146A) and light yellow-green (RHS 145B) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

The female parent of 'PHALFOTJ', cultivar '01-1698' (unpatented), is no longer in existence, therefore a meaningful comparison cannot be made.

'PHALFOTJ' differs from male parent plant '20421-01' (unpatented) in that 'PHALFOTJ' has rhombic apical lobes and weakly spatulate lateral lobes, whereas '20421-01' has triangular apical lobes and spatulate lateral lobes. Additionally, 'PHALFOTJ' has smaller flowers, narrower apical lobes, and shorter whiskers than '20421-01'.

'PHALFOTJ' is most similar to the commercial *Phalaenopsis* plants named 'PHALBOCIQ' (unpatented) and 'CHUNLI' (unpatented). 'PHALFOTJ' differs from the commercial variety 'PHALBOCIQ' in that 'PHALFOTJ' has rhombic apical lobes, weakly spatulate lateral lobes, and a shaded flower pattern, whereas 'PHALBOCIQ' has triangular apical lobes, spatulate lateral lobes, and a center flower pattern. Additionally, 'PHALFOTJ' has shorter whiskers and smaller flowers than 'PHALBOCIQ'.

'PHALFOTJ' differs from the commercial variety 'CHUNLI' in that 'PHALFOTJ' has rhombic apical lobes and a shaded flower pattern, whereas 'CHUNLI' has ovate apical lobes and a striped flower pattern. Additionally, 'PHALFOTJ' has longer whiskers and larger flowers than 'CHUNLI'.

I claim:

1. A new and distinct variety of *Phalaenopsis* plant named 'PHALFOTJ', substantially as described and illustrated herein.

* * * * *